(12) United States Patent
Igari et al.

(10) Patent No.: US 8,648,922 B2
(45) Date of Patent: Feb. 11, 2014

(54) MEDICAL IMAGE APPARATUS AND MEDICAL IMAGE ARCHIVING APPARATUS

(75) Inventors: Satoshi Igari, Utsunomiya (JP); Hiroki Saito, Otawara (JP)

(73) Assignees: Kabushiki Kaisha Toshiba, Tokyo (JP); Toshiba Medical Systems Corporation, Tochigi-Ken (JP)

(*) Notice: Subject to any disclaimer, the term of this patent is extended or adjusted under 35 U.S.C. 154(b) by 187 days.

(21) Appl. No.: 13/179,176

(22) Filed: Jul. 8, 2011

(65) Prior Publication Data

US 2012/0014661 A1   Jan. 19, 2012

(30) Foreign Application Priority Data

Jul. 13, 2010  (JP) .................................. 2010-159110
Jun. 21, 2011  (JP) .................................. 2011-136849

(51) Int. Cl.
*H04N 5/232*   (2006.01)

(52) U.S. Cl.
USPC ....................... 348/211.2; 348/333.12; 348/77

(58) Field of Classification Search
USPC .................... 348/211.2, 211.9, 240.2, 333.12
See application file for complete search history.

(56) References Cited

U.S. PATENT DOCUMENTS

| 7,944,478 | B2 * | 5/2011 | Shiibashi et al. | 348/211.2 |
| 8,065,166 | B2 * | 11/2011 | Maresh et al. | 705/3 |
| 2002/0091659 | A1 * | 7/2002 | Beaulieu et al. | 706/62 |
| 2008/0021834 | A1 * | 1/2008 | Holla et al. | 705/51 |

FOREIGN PATENT DOCUMENTS

| JP | 5-161634 A | 6/1993 |
| JP | 2000-175897 A | 6/2000 |
| JP | 2006-6449 A | 1/2006 |
| JP | 2008-264254 A | 11/2008 |
| JP | 2009-122599 A | 6/2009 |
| JP | 2009-254690 A | 11/2009 |

* cited by examiner

*Primary Examiner* — Gevell Selby
(74) *Attorney, Agent, or Firm* — Yoshida & Associates, LLC

(57) ABSTRACT

A medical image apparatus according to the embodiments has a medical image utilization apparatus and medical image archiving apparatus. The former has an acquisition part that acquires a requested frame rate for cases in which medical images are movie displayed on its display, and an designating part that designates an attention point with respect to one of the medical images displayed. The latter has a transmission speed measurement part that measures the data transmission speed between the former and the latter, an extraction part that, based on the requested frame rate, the attention point and the data transmission speed, extracts the region including the attention point for each of the medical images, and a transmission part that transmits an image of the extracted region to the display. The display displays, as a moving image, the images of the region extracted by said extraction part at said requested frame rate.

10 Claims, 12 Drawing Sheets

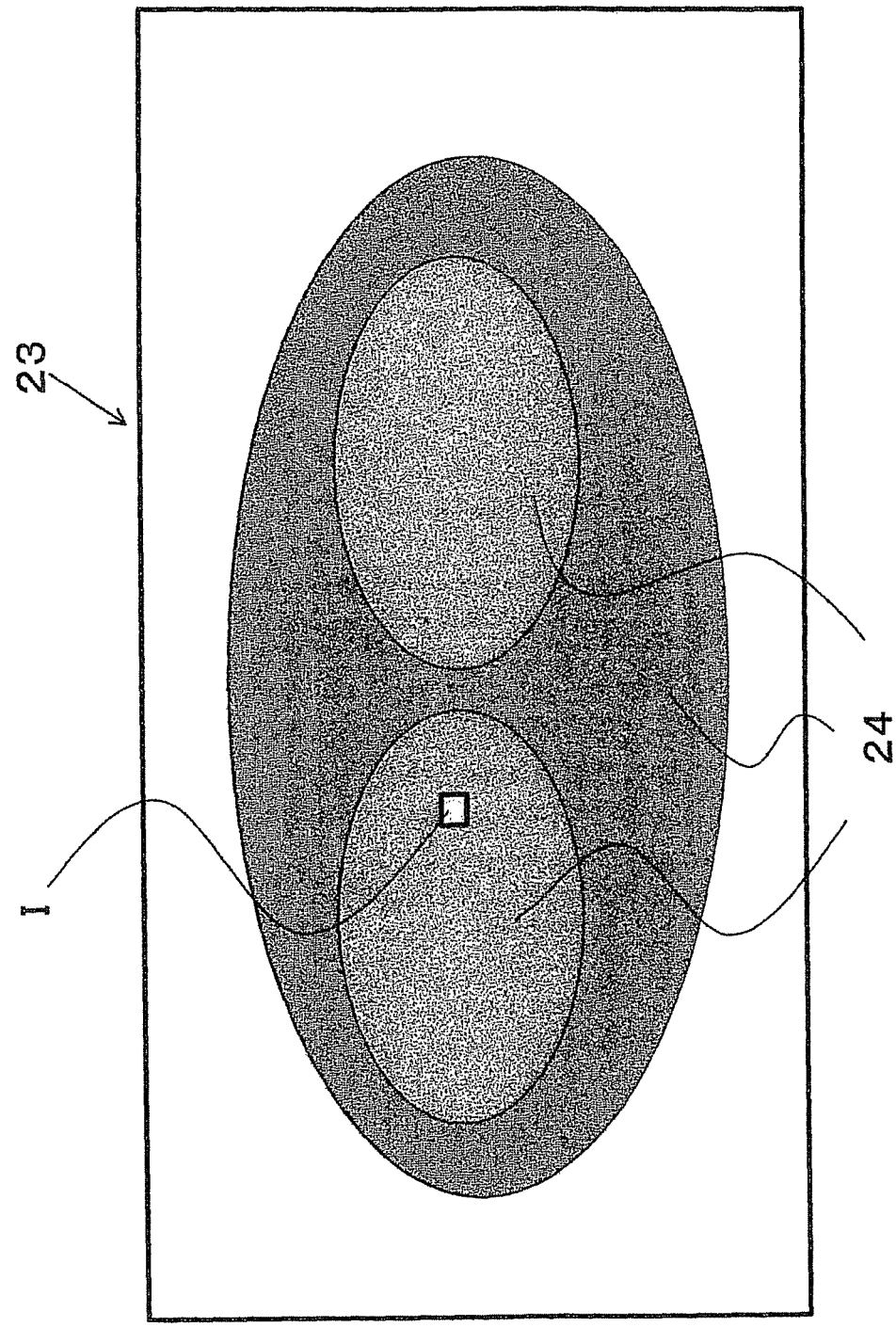

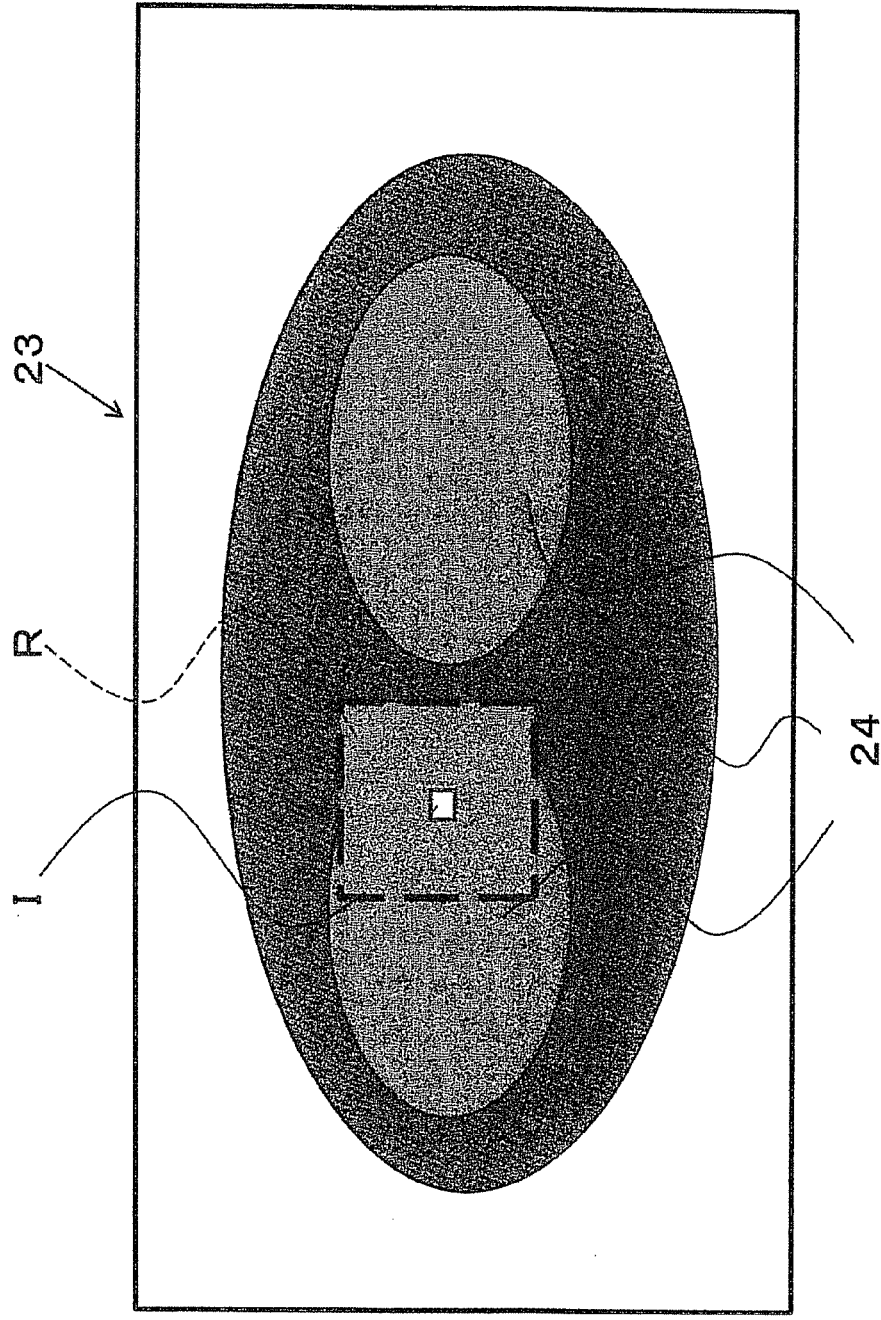

MEDICAL IMAGE APPARATUS AND MEDICAL IMAGE ARCHIVING APPARATUS

CROSS-REFERENCE TO RELATED APPLICATION

This application is based upon and claims the benefit of priority from Japanese Patent Application No. 2010-159110, filed Jul. 13, 2010 and Japanese Patent Application No. 2011-136849, filed Jun. 21, 2011; the entire contents of which are incorporated herein by reference.

FIELD

The embodiment of the present invention relates to a medical image apparatus and medical image archiving apparatus.

BACKGROUND

Generally, images taken with medical imaging apparatuses such as X-ray imaging apparatus, X-ray CT scanners, and MRI (magnetic resonance imaging) diagnostic apparatus are recorded on a medical image archiving apparatus (servers) inside a hospital. The images, based on requests by radiographic interpreters, etc., are displayed on medical image utilization apparatuses (viewers) inside the hospital and outside the hospital (doctor's homes, etc.), from the servers inside hospitals, via LAN cables, wireless LAN, the Internet, etc.

On the other hand, there are cases in which low-performance simple terminals are used as a medical image utilization apparatus.

Moreover, there are cases in which a medical image utilization apparatus is utilized through a network with a slow line speed.

BRIEF DESCRIPTION OF THE DRAWINGS

FIG. 4A is a supplementary diagram of the flowchart according to the first embodiment.

FIG. 4B is a supplementary diagram of the flowchart according to the first embodiment.

DETAILED DESCRIPTION

The medical image apparatus according to the embodiments has a medical image utilization apparatus and medical image archiving apparatus. Moreover, the medical image utilization apparatus has an acquisition part that acquires a requested frame rate for cases in which a plurality of medical images taken with the medical image apparatus are movie displayed on a display of the medical image utilization apparatus, and a designating part that designates an attention point with respect to one of the plurality of medical images displayed on the display. Furthermore, the medical image archiving apparatus has a transmission speed measurement part that measures the data transmission speed between the medical image utilization apparatus and the medical image archiving apparatus, an extraction part that extracts an region including the attention point for each of the plurality of medical images, based on the requested frame rate, the attention point, and the data transmission speed, and a transmission part that transmits an image of the region extracted by the extraction part to the display. Moreover, the display displays, as a moving image, the images of the region extracted by said extraction part at said requested frame rate.

(Apparatus Configuration)

Figure 1:
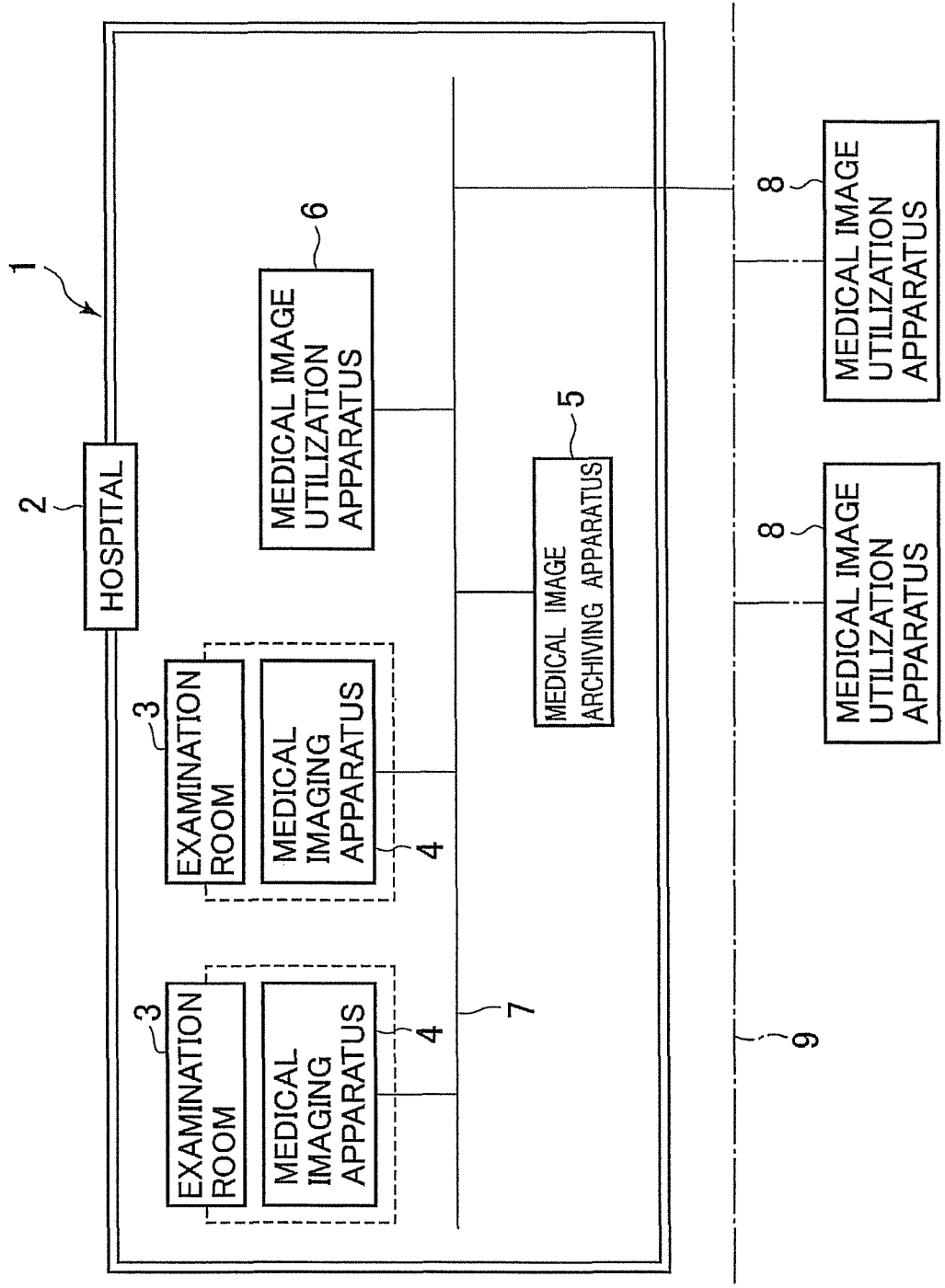
FIG. 1 is a outside drawing of a medical image system that includes a medical image apparatus according to the first, second or fifth embodiment.

First, using FIG. 1, the configuration of a medical imaging system 1, which is common for the first to third embodiments, is explained.

As shown in FIG. 1, inside a hospital 2, there are multiple examination rooms 3. Inside each examination room 3, medical imaging apparatuses 4 such as X-ray imaging apparatus, an X-ray CT scanner, and an MRI apparatus are disposed.

Moreover, inside the hospital 2, a medical image archiving apparatus 5 (hereinafter may be referred to as a "server") that stores medical images acquired with the medical imaging apparatuses 4 is disposed.

Moreover, inside the hospital 2, a medical image utilization apparatus 6 that can display the medical images acquired with the medical imaging apparatus 4 or the medical images stored in the medical image archiving apparatus 5 is disposed.

These apparatuses inside the hospital 2 are constituted such that communications can be established through an in-hospital network 7.

Image communications between these apparatuses comply with the DICOM (Digital Imaging and Communications in Medicine) standard. Moreover, not limited to DICOM, any existing standard may also be applied.

Moreover, outside the hospital 2 (for example, at radiographic interpreters' homes), medical image utilization apparatuses 8 that can display the medical images acquired with the medical imaging apparatus 4 or the medical images stored in the medical image archiving apparatus 5 are disposed. For the medical image utilization apparatuses 8, compared to the medical image utilization apparatus 6, there are many cases in which they are low performance devices, such as devices with slow processing speed.

These medical image utilization apparatuses 8 located outside hospitals can communicate with each device connected on the in-hospital network 7 through an extramural network 9. The extramural network 9 is a network having a line speed slower than the in-hospital network 7.

The medical imaging system 1 is configured from the abovementioned examination rooms 3, the medical imaging apparatus 4, the medical image archiving apparatus 5, the medical image utilization apparatus 6, the medical image utilization apparatuses 8, the in-hospital network 7, and the extramural network 9.

Moreover, in the present specifications, the medical image archiving apparatus 5, the medical image utilization apparatus 6, and/or the medical image utilization apparatuses 8 may be collectively referred to as a "medical image apparatus."

Further, the medical image utilization apparatus 6 and/or the medical image utilization apparatus 8 may be referred to as a "viewer."

(First Embodiment)

Using FIG. 2 to FIG. 4B, the configuration of a medical image apparatus according to the first embodiment is described in detail.

Figure 2:
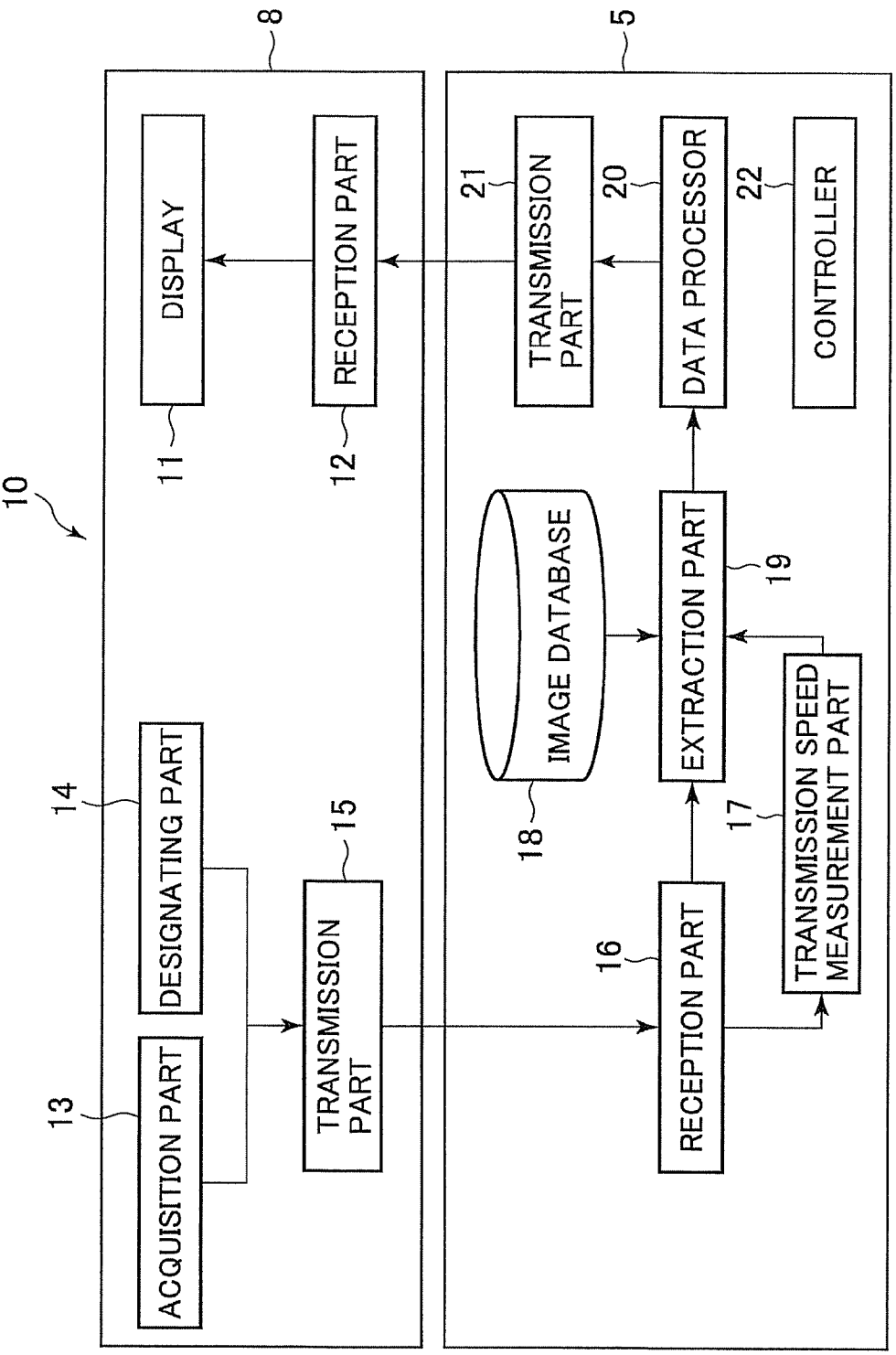
FIG. 2 is a block diagram showing a relationship between components according to the first embodiment.

FIG. 2 is a figure showing the configuration of a medical image apparatus 10 made up of the medical image archiving apparatus 5 and the medical image utilization apparatus 8. Moreover, the medical image utilization apparatus 6 has a similar configuration to the medical image utilization apparatus 8.

(Configuration of the Medical Image Utilization Apparatus)

The medical image utilization apparatus 8 has a display 11; a reception part 12; an acquisition part 13; a designating part 14; and a transmission part 15.

The display 11 displays medical images taken with the medical imaging apparatus 4. The medical images, for example, are transmitted from the medical image archiving apparatus 5 (an image database 18 to be explained subsequently) through the reception part 12.

The acquisition part 13 acquires a frame rate for cases in which a plurality of medical images taken with the medical imaging apparatus 4 are movie displayed on the display 11. For example, using an input means, not shown in the figures, the acquisition part 13 acquires the frame rate based on the input of specific numerical values (for example, 40 fps) by a radiographic interpreter. The frame rate acquired may be hereinafter referred to as a "requested frame rate."

Moreover, "movie" in the present specifications refers to any display mode that sequentially present a plurality of medical images, such as a cine display (a display method for switching a plurality of still images one by one) and a display based on movie files created in such as MPEG format. Below, cases of the cine display are explained.

The designating part 14 designates an attention point with respect to one of the plurality of medical images displayed on the display 11. The attention point is designated while the radiographic interpreter observes the medical images displayed on the display 11 and inputs the position information of a noteworthy point, using input means not shown in the figures. For example, an XY coordinate value of the attention point in a medical image is input using an input means, such as a keyboard. Or, the coordinate value of the position designated may be calculated by operating an input means, such as a mouse, and by designating the attention point in the medical images with a pointer.

The requested frame rate acquired at the acquisition part 13 and the information of the attention point designated at the designating part 14 are transmitted through the transmission part 15 to the medical image archiving apparatus 5.

In the present embodiment, the information (coordinate values) regarding the attention point designated by the designating part 14 is transmitted to the medical image archiving apparatus 5, and at the same time, it is stored in a storage part, not shown in the figures, provided inside the medical image utilization apparatus 8. The information is utilized for position adjustment, etc., when the medical images are displayed on the display 11. Moreover, it is also possible to use a method for managing the information on the server side.

(Configuration of the Medical Image Archiving Apparatus)

The medical image archiving apparatus 5 has a reception part 16; a transmission speed measurement part 17; an image database (database) 18; an extraction part 19; a data processor 20; a transmission part 21; and a controller 22.

The reception part 16 receives the requested frame rate and the information of the attention point transmitted from the transmission part 15 of the medical image utilization apparatus 8. Moreover, the reception part 16 transmits the received information to the transmission speed measurement part 17 and the extraction part 19.

The transmission speed measurement part 17 measures the data transmission speed of the medical images between the medical image utilization apparatus 8 and the medical image archiving apparatus 5.

The data transmission speed refers to the speed for transmitting medical images from the transmission part 21, which is explained subsequently, to the reception part 12. The transmission speed measurement part 17 measures the data transmission speed for cases in which it receives information such as the requested frame rate acquired at the acquisition part 13 from the reception part 16. This measurement is explained in detail subsequently. The data transmission speed that is measured is transmitted to the extraction part 19. Moreover, for the data transmission speed, values recorded in advance in the storage part, not shown in the figures, etc., inside the medical image archiving apparatus 5, may be used.

The image database 18 stores the medical images taken with the medical imaging apparatus 4. The stored medical images are read out based on an input command from the radiographic interpreter and displayed on the display 11 of a viewer. Or, the stored medical images are utilized for extraction processing in the extraction part 19, which is explained subsequently.

Based on the requested frame rate acquired at the acquisition part 13, the attention point designated by the designating part 14, and the data transmission speed measured by the transmission speed measurement part 17, the extraction part 19 extracts the region (hereinafter may be referred to as the "extraction region") including the attention point in the medical images that are refreshed at the requested frame rate when the plurality of medical images are movie displayed. Extraction processing is performed for all of the plurality of images that constitute the movie. Extraction processing by the extraction part 19 is explained in detail subsequently.

Moreover, it is not necessary to perform extraction processing on all of the plurality of images that constitute the movie. For example, for the medical image utilization apparatus 8, for cases in which the images to be used for the movie display are designated (for example, if there are 100 images that are taken, designate from the 20th image to the 50th image), it is possible for the extraction part 19 to perform extraction processing for these designated images only.

The data processor 20 performs processing to sequentially transmit the medical images of the extraction region extracted by the extraction part 19, while maintaining the resolution during image taking (high resolution), through the transmission part 21 to the display 11. Moreover, the data processor 20, after converting the medical images of the region other than the extraction region (hereinafter may be referred to as a "non-extraction region") to a low resolution to the degree that image refreshing of the extraction region is not affected (lower resolution than during image taking), performs processing to sequentially transmit them through the transmission part 21 to the display 11. Moreover, for cases in which processing to sequentially transmit the medical images to the display 11 is performed, the data processor 20 also performs processing to associate the extraction region with the non-extraction region of each medical image.

The controller 22 carries out the action control of each site of the medical image archiving apparatus 5. For example, it carries out the action control of the transmission part 21 so as to transmit the image of the region extracted by the extraction part 19 to the display 11.

Moreover, for cases in which movie files such as MPEG are used as medical images, first, movie file data is loaded on a memory (not shown in the figures) inside the medical image archiving apparatus 5 and divided into a plurality of images to movie display. Subsequently, extraction processing is performed for each image divided by the extraction part 19.

Figure 3:
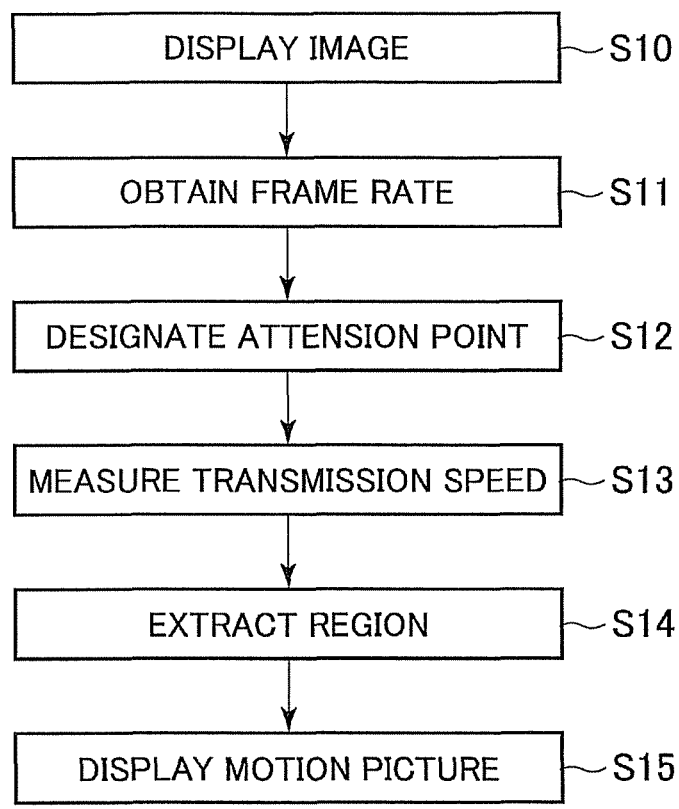
FIG. 3 is a flowchart showing an outline of processing according to the first embodiment.

Next, using FIG. 3 to FIG. 4B, the action of the medical image apparatus according to the first embodiment is explained in detail.

When a radiographic interpreter requests medical images regarding a certain subject from the medical image utilization apparatus 8, which is located at home, etc. through the extramural network 9, the image database 18 transmits part of the medical images that meet the request (part of the plurality of medical images) to the medical image utilization apparatus 8. As a result, the part of the medical images is displayed as still images (S10) on the display 11 of the medical image utilization apparatus 8.

Next, the radiographic interpreter, through the input means, not shown in the figures, etc., inputs the desired frame rate for the medical images to be movie displayed on the display 11. The acquisition part 13 acquires the input value as the requested frame rate (S11).

Moreover, the radiographic interpreter, while viewing the still images displayed at S10, through the input means not shown in the figures, etc., inputs the section that the radiographic interpreter would specifically like to observe (attention point). The designating part 14 designates the attention point for the still image, based on the input (S12). The state in which the attention point is designated in the still image is shown in FIG. 4A. To a still image 23 displayed on the display 11, a tomographic image of a subject 24 is depicted. Moreover, an attention point I that the designating part 14 designates in it is displayed. Note that for S11 and S12, either step can be performed before the other.

Next, the transmission speed measurement part 17 provides a command to the controller 22 so as to transmit some of the plurality of medical images that constitute the movie from the image database 18 to the medical image utilization apparatus 8, for cases in which it receives information such as the requested frame rate acquired at the acquisition part 13 from the reception part 16. Based on the command, the controller 22 carries out the control of the transmission part 21 so as to transmit the medical images to the medical image utilization apparatus 8. Moreover, the transmission speed measurement part 17 measures the data transmission speed of the medical images between the medical image utilization apparatus 8 and the medical image archiving apparatus 5 (data transmission speed between the transmission part 21 and the reception part 12) (S13). The data transmission speed measured is transmitted to the extraction part 19.

Moreover, the extraction part 19, when it receives the requested frame rate acquired by the acquisition part 13, the attention point designated by the designating part 14, and the data transmission speed measured by the transmission speed measurement part 17, starts processing to extract the region to be displayed at the requested frame rate when the plurality of medical images are movie displayed based on the information (S14).

Extraction processing is explained here, for example, for cases in which a square region is extracted from the image data with 32-bit color. Here, by setting the length of one side of the square as "a" (pixel), the requested frame rate as "F" (fps), and the data transmission speed as "B" (bps), the following formula (1) is established.

[Formula 1]

$$a^2 \times 32 \times F = B \qquad (1)$$

According to formula (1), the length "a" of one side of the square is $\sqrt{(B/32F)}$(pixel). That is, when the medical images are movie displayed, the size (area) of the region refreshed at the requested frame rate is $\sqrt{(B/32F)} \times \sqrt{(B/32F)}$.

Based on the relationship between this size and the attention point I, the position of the region is determined, including the attention point in the medical image on which the image refreshing is performed at the requested frame rate when the medical images are movie displayed. For example, in FIG. 4A, the region is extracted as the extraction region by determining the square region in the range of a/2 to the top, bottom, left and right, centered on the attention point I.

One example of the determined square region is shown in FIG. 4B. To the still image 23 displayed on the display 11, the tomographic image of the subject 24 is provided. Moreover, a region R centered at the attention point I designated by the designating part 14 is displayed.

Further, FIG. 4B is provided for convenience of explanation purposes, but in reality, the region R extracted from each of the plurality of medical images is movie displayed, according to the requested frame rate.

Moreover, if the number of pixels in the region in which the image refreshing is performed at the requested frame rate is the same, the shape of the region to be extracted is not limited to a square.

Extraction processing is performed with respect to all of the plurality of images constituting the movie. The image of the extraction region is sequentially transmitted, based on the control by the controller 22, through the transmission part 21, to the display 11.

Moreover, after being converted to low resolution by the data processor 20, the image of the non-extraction region is associated with the image of the extraction region and transmitted sequentially through the transmission part 21 to the display 11. The display 11 performs movie display (cine display) by sequentially displaying the images that are sequentially transmitted (S15). Moreover, it is also possible that the controller 22 carries out the control of the display 11 so as to perform image refreshing of the extraction region at the requested frame rate.

As above, according to the present embodiment, with regard to the extraction region, it is possible to observe high resolution movie ages at the requested frame rate. That is, when the images are transmitted, by limiting the images that are transmitted in high resolution to the extraction region only, it is possible to movie display the extraction region including the attention point at the frame rate requested by the radiographic interpreter. Therefore, even for cases in which low performance terminals or low line speed network are used, smooth radiographic image interpretation is possible, leading to diagnostic support.

(Second Embodiment)

Figure 5:
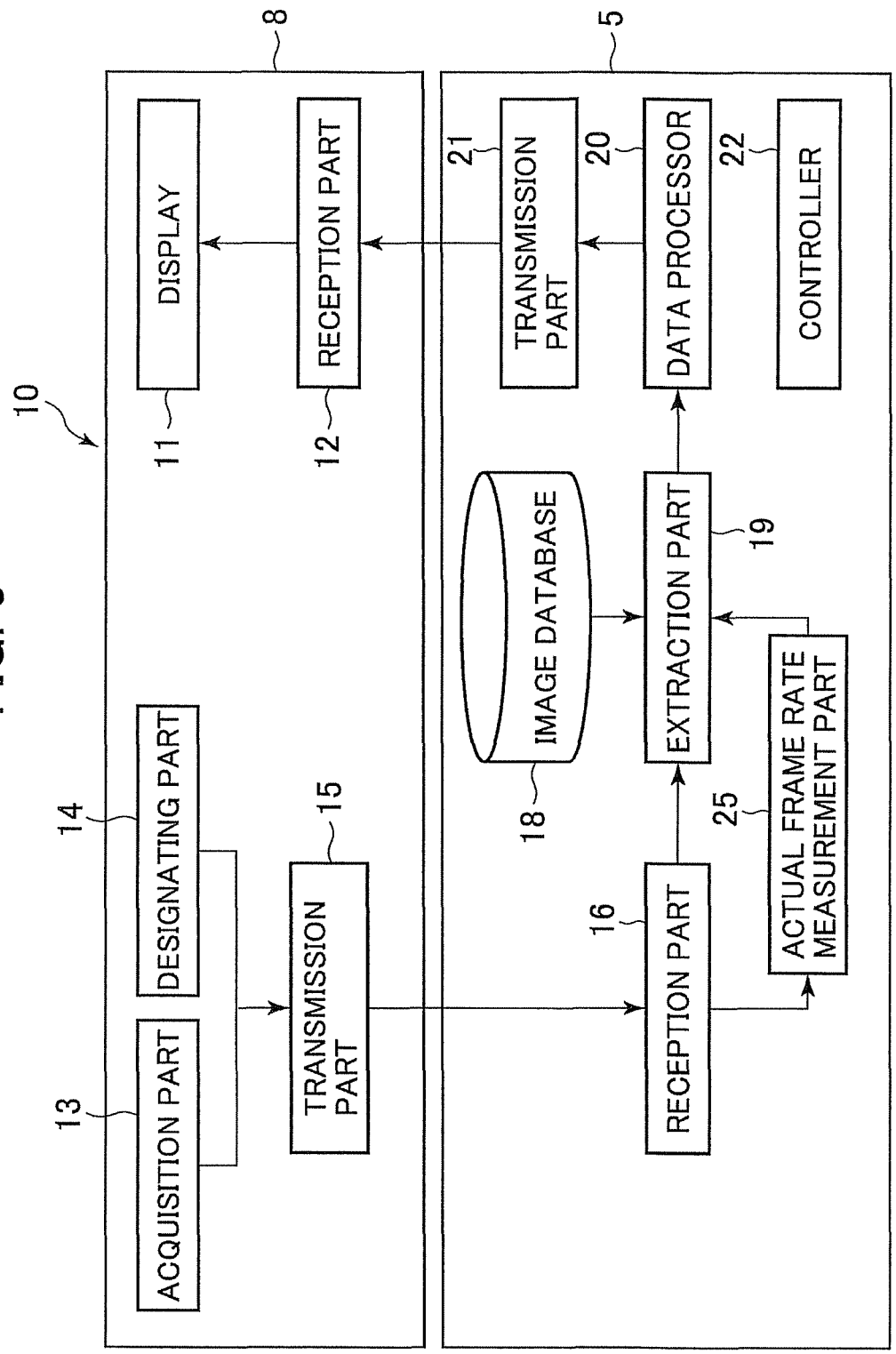
FIG. 5 is a block diagram showing a relationship between components according to the second embodiment.
Figure 6:
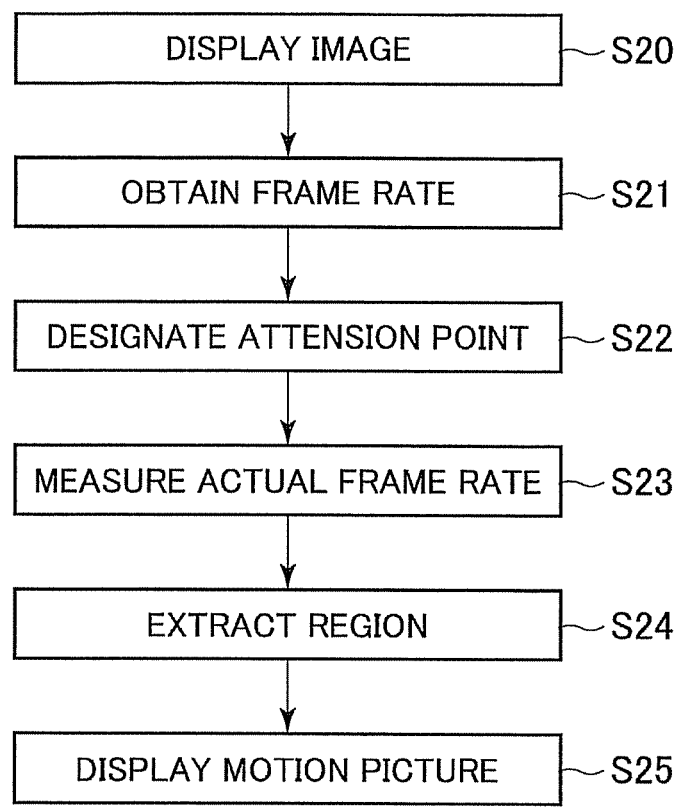
FIG. 6 is a flowchart showing an outline of processing according to the second embodiment.

Next, using FIG. 5 and FIG. 6, the configuration of the medical image apparatus according to the second embodiment is explained in detail. Note that an explanation of the configuration, which is similar to the first embodiment, is omitted.

The second embodiment is different from the first embodiment in that, for cases in which the region displayed at the requested frame rate is extracted, an actual frame rate is used instead of the data transmission speed.

Therefore, for the second embodiment, as shown in FIG. 5, an actual frame rate measurement part 25 is provided inside the medical image archiving apparatus 5.

The actual frame rate measurement part 25 measures the actual frame rate for the case in which the movie display is actually performed on the display 11 of the medical image utilization apparatus 8,. Here, the "actual frame rate" refers to a value showing how many times the medical images transmitted from the medical image archiving apparatus 5 are refreshed in reality on the display 11 each second. The measurement processing by the actual frame rate measurement part 25 is described in detail subsequently. The data transfer speed that is measured is transmitted to the extraction part 19.

Moreover, the actual frame rate measurement part 25 may be provided inside the medical image utilization apparatus 8. In such cases, when information such as the requested frame rate is transmitted from the transmission part 15 to the medical image archiving apparatus 5, the information is also transmitted to the actual frame rate measurement part 25. The actual frame rate measurement part 25 measures the actual frame rate on the display 11, with the transmission of the information as the trigger. Moreover, the actual frame rate measurement part 25 transmits the value of the actual frame rate that is measured through the transmission part 15 to the extraction part 19.

Next, using FIG. 6, the action of the medical image apparatus according to the second embodiment is described in detail.

For cases in which a radiographic interpreter requests medical images regarding a certain subject from the medical image utilization apparatus 8, which is located at home, etc., the image database 18 transmits part of the medical images that meet the request (part of the plurality of medical images) to the medical image utilization apparatus 8 through the extramural network 9. As a result, the part of the medical images is displayed as a movie (S20) on the display 11 of the medical image utilization apparatus 8.

Next, through the input means, not shown in the figures, etc., the radiographic interpreter inputs the desired frame rate for the medical images to be movie displayed on the display 11. The acquisition part 13 acquires the input value as the requested frame rate (S21).

Moreover, the radiographic interpreter specifies sections that the radiographic interpreter would particularly like to observe (attention point), while viewing the movie displayed at S20. After the attention point is specified, the display 11 displays one of the still images constituting the movie based on the command from the radiographic interpreter. The radiographic interpreter inputs the attention point on the still image through the input means, not shown in the figures, etc. The designating part 14 designates the attention point for the still image (S22) based on the input. Note that for S21 and S22, either step may be performed before the other.

Next, when receiving information from the reception part 16 such as the requested frame rate acquired at the acquisition part 13, the actual frame rate measurement part 25 sends a command to the display 11 so as to perform the movie display performed at S20 again. Based on the command, the movie display is performed at the display 11.

During the movie display, the actual frame rate measurement part 25 calculates the actual frame rate by measuring how many image refreshing are performed each second (S23). The actual frame rate that is measured is transmitted to the extraction part 19.

Moreover, the extraction part 19 receives the requested frame rate that is acquired by the acquisition part 13, the attention point that is designated by the designating part 14, and the frame rate measured by the actual frame rate measurement part 25, and, based on the information, starts processing to extract the regions displayed at the requested frame rate that is applied to the movie display of the plurality of medical images (S24).

With regard to the extraction processing at S24, for example, a method is used by which the optimal size of the extraction region is determined with changing the size of the extraction region centered at the attention point (a method using, the so-called, a binary search algorithm).

Specifically, first, the extraction part 19 sets the search range of the extraction region (maximum to minimum) and designates the intermediary value in the specified range as the temporary extraction region. Next, the medical image utilization apparatus 8 displays the temporary extraction region on the display 11, and transmits the actual frame rate that is measured at the actual frame rate measurement part 25 at that time to the medical image archiving apparatus 5. The extraction part 19 compares the actual frame rate that is transmitted and the requested frame rate (for example, the requested frame rate ±10%). Here, when the compared values match, it is determined that the temporary extraction region set in advance by the extraction part 19 is the extraction region to be calculated.

On the other hand, for example, for cases in which the value of the actual frame rate is larger than the value of the requested frame rate, for the extraction part 19, the search range is set again between the intermediary value and the minimum value, and the intermediary value in the search range that is set again as the temporary extraction region. The temporary extraction region that is set again is displayed on the display 11, and the actual frame rate that is measured by the actual frame rate measurement part 25 at that time is transmitted to the medical image archiving apparatus 5. Moreover, the extraction part 19 performs processing to compare the actual frame rate that is transmitted and the requested frame rate (the requested frame rate ±10%).

In this way, the same processing is repeated until the actual frame rate and the requested frame rate match, thereby the extraction region is determined. Note that when the actual frame rate changes, resulting from changes in the network bandwidth, etc., it is possible to extract the optimal region by performing the above extraction processing again.

Extraction processing is performed with respect to all of the plurality of images constituting the movie. The images of the extraction region, based on the control by the controller 22, are transmitted sequentially through the transmission part 21 to the display 11. Moreover, after they are converted to low resolution by the data processor 20, the images of the non-extraction region is associated with the images of the extraction region and sequentially transmitted through the transmission part 21 to the display 11. The display 11 performs the movie display (cine display) by sequentially displaying the images that are sent sequentially (S25).

As above, according to the present embodiment, the region refreshed at the requested frame rate is extracted based on the actual frame rate for the display 11. That is, it is possible to extract the refreshed region based on the display performance of the display 11 on which the movie display is actually performed. Therefore, even for cases in which low performance terminals and low line speed networks are used, smooth radiographic image interpretation is possible, leading to diagnostic support.

(Third Embodiment)

Figure 7:
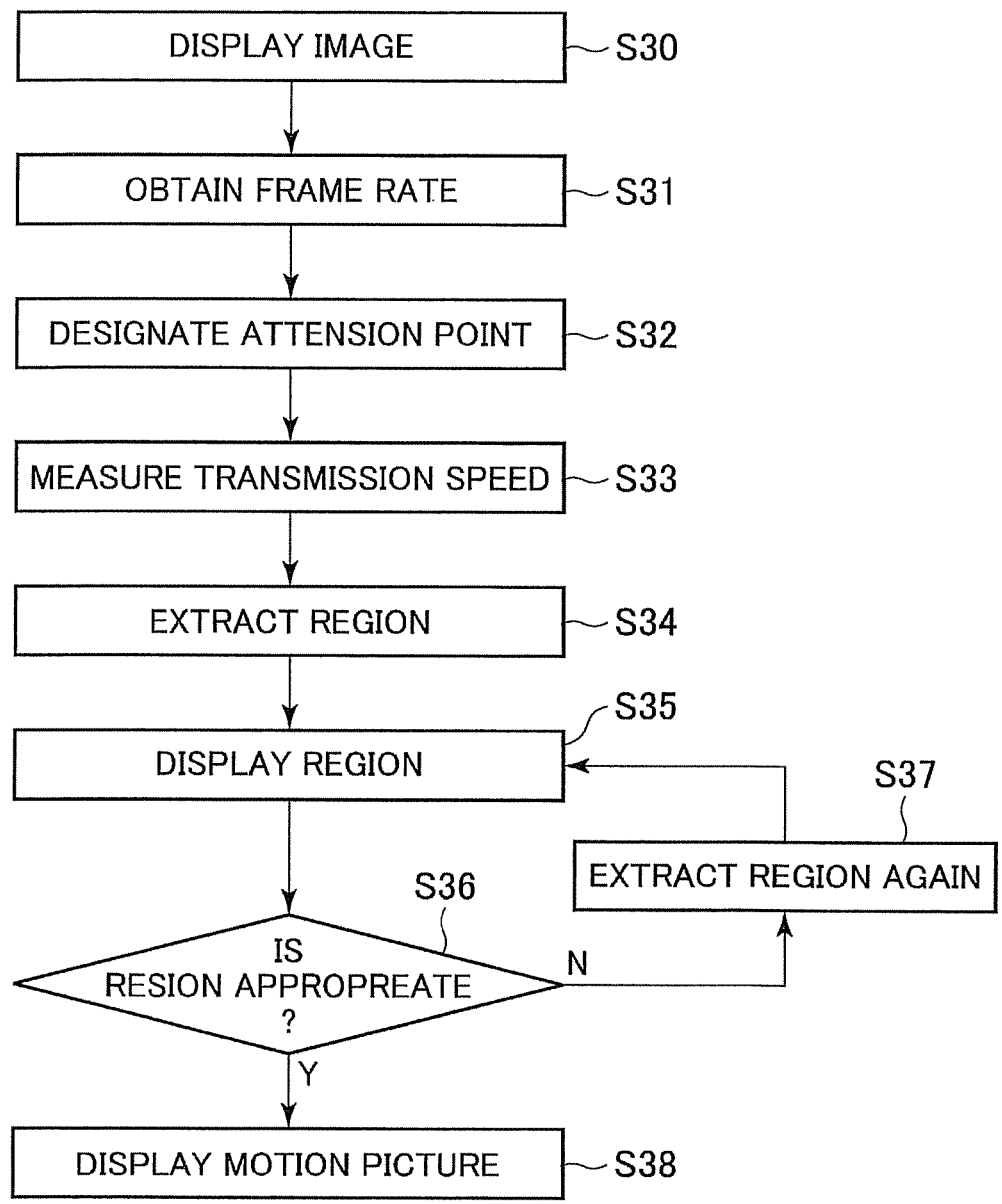
FIG. 7 is a flowchart showing an outline of processing according to the third embodiment.

Next, using FIG. 7, processing according to the third embodiment is described in detail.

In the first and second embodiments, when image refreshing of the predefined region is performed at the requested frame rate, before starting the image refreshing, there are cases in which a radiographic interpreter would like to verify whether or not the predefined region is within the region desired by the radiographic interpreter. The third embodiment relates to the processing to satisfy this type of request.

Note that processing from the first embodiment is explained below as a basis; however, the processing of the present embodiment is also applicable to the second embodiment.

When a radiographic interpreter requests medical images regarding a certain subject from the medical image utilization apparatus 8, which is located at home, etc., the image database 18 transmits part of the medical images that meet the request (part of the plurality of medical images) to the medical image utilization apparatus 8 through the extramural network 9. As a result, the part of the medical images is displayed as still images (S30) on the display 11 of the medical image utilization apparatus 8.

Next, through the input means, not shown in the figures, etc., the radiographic interpreter inputs the desired frame rate for the medical image to be movie displayed on the display 11. The acquisition part 13 acquires the input value as the requested frame rate (S31).

Moreover, while viewing the still images displayed at S30, through the input means, not shown in the figures, etc., the radiographic interpreter inputs the section that the radiographic interpreter would specifically like to observe (attention point). The designating part 14 designates the attention point for the still image, based on the input (S32).

Next, for cases in which it receives information from the reception part 16 such as the requested frame rate acquired at the acquisition part 13, the transmission speed measurement part 17 measures the data transmission speed of the medical images between the medical image utilization apparatus 8 and the medical image archiving apparatus 5 (data transmission speed between the transmission part 21 and the reception part 12) (S33). The data transmission speed that is measured is transmitted to the extraction part 19.

Moreover, when it receives the requested frame rate acquired by the acquisition part 13, the attention point that is designated by the designating part 14, and the data transmission speed that is measured by the transmission speed measurement part 17, the extraction part 19, based on the information, starts processing to extract the region to be displayed at the requested frame rate when the plurality of medical images are movie displayed (S34). For the specific extraction processing, since it is the same as the first embodiment, an explanation is omitted.

The medical images of the extraction region are transmitted to the display 11 through the transmission part 21, based on the control by the controller 22. Moreover, the medical images in the non-extraction region, after being converted to low resolution by the data processor 20, are transmitted through the transmission part 21 to the display 11. The display 11 displays where the extraction region is positioned on the medical images (S35). As the display form, for example, a frame showing the range of the extraction region on the still image displayed on the display 11 is displayed.

The radiographic interpreter who viewed the display by S35 determines whether or not the extraction region is appropriate (S36).

When the radiographic interpreter determines that it is appropriate (for cases of Y at S36), the radiographic interpreter, through the input means, not shown in the figures, etc., inputs in order to say it is appropriate. Based on the input, the extraction part 19 performs the same extraction processing for all of the images constituting the movie. The images of the extraction region, based on the control by the controller 22, are sequentially transmitted through the transmission part 21 to the display 11. Moreover, the images of for the non-extraction region, after they are converted to low resolution at the data processor 20, they are associated with the images of the extraction region and sequentially transmitted through the transmission part 21 to the display 11. The display 11 performs the movie display (cine display) by sequentially displaying the images that are transmitted sequentially (S38).

On the other hand, when the radiographic interpreter determines that it is not appropriate (for cases of N at S36), the radiographic interpreter newly performs such as input of the requested frame rate.

According to the input, the acquisition part 13 performs acquisition of the new requested frame rate, etc. Moreover, the extraction part 19, based on the new requested frame rate, etc., performs re-extraction of the extraction region (S37).

The region that is re-extracted is displayed on the display 11, based on the action control by the controller 22 (S35).

By repeating the actions from S35 to S37, it is possible to refresh at the frame rate requested by the radiographic interpreter and in the refreshed region requested.

As above, according to the present embodiment, before the movie is displayed, it can be determined whether or not the region refreshed at the requested frame rate matches the request from the radiographic interpreter. Therefore, the movie display meeting the request of the radiographic interpreter can be achieved promptly.

(Fourth Embodiment)

Figure 8A:
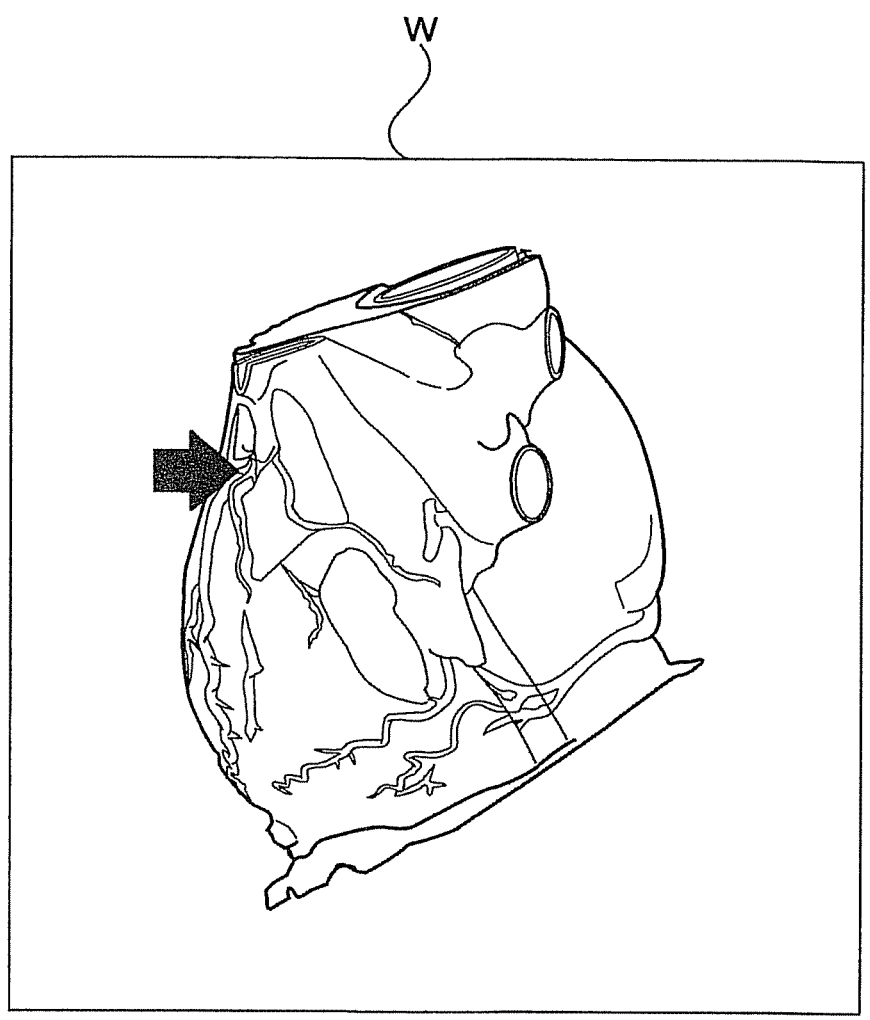
FIG. 8A is an example of a volume rendering image used in explanation of the fourth embodiment.
Figure 9:
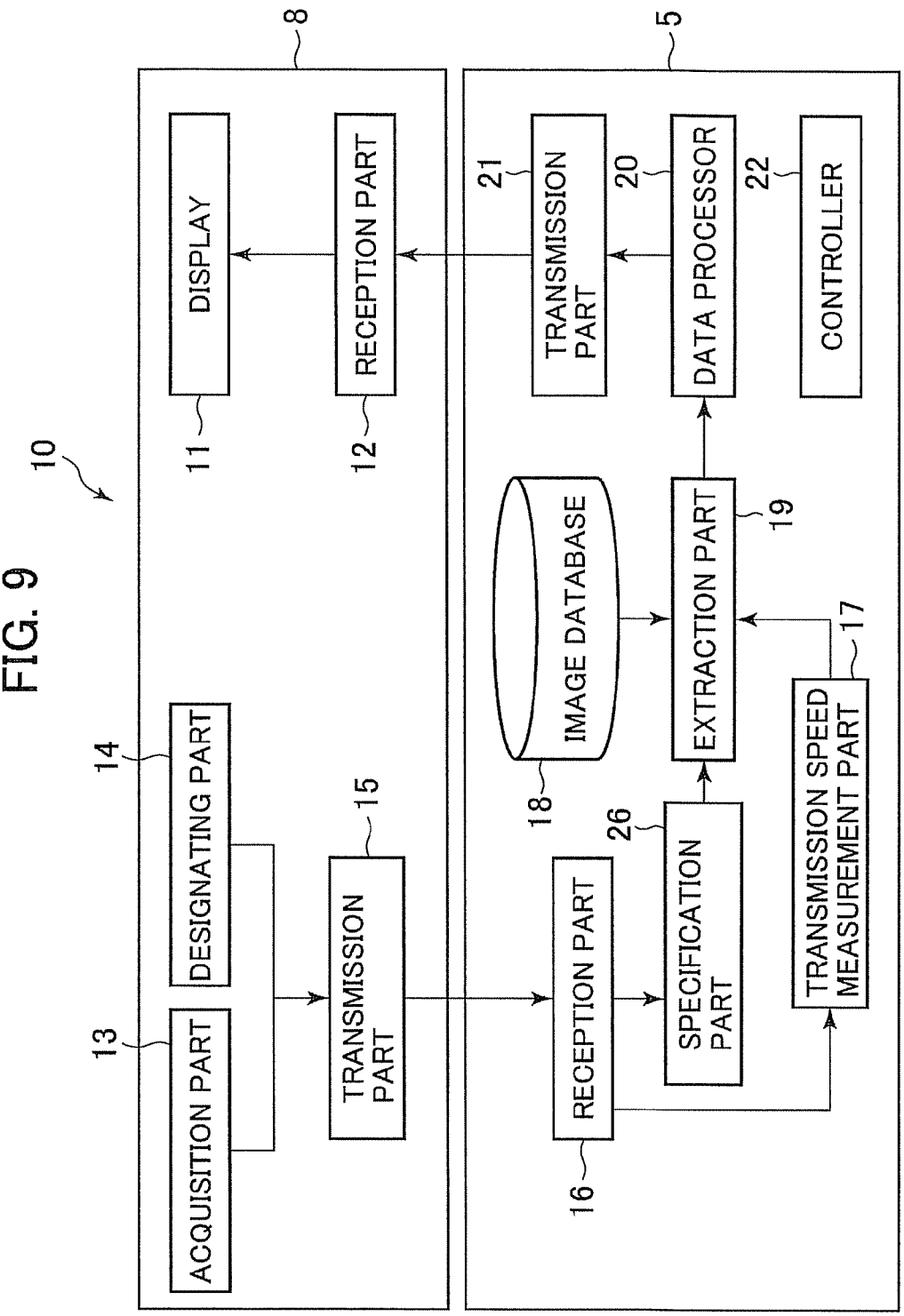
FIG. 9 is a block diagram showing a relationship between components according to the fourth embodiment.

Next, using FIG. 8A and FIG. 9, processing according to the fourth embodiment is explained in detail. Note that processing from the first embodiment is explained below as a basis; however, the configuration of the present embodiment is also applicable to the second embodiment and the third embodiment. Moreover, an explanation for the configuration, which is the same as the first embodiment, is omitted.

Figure 8B:
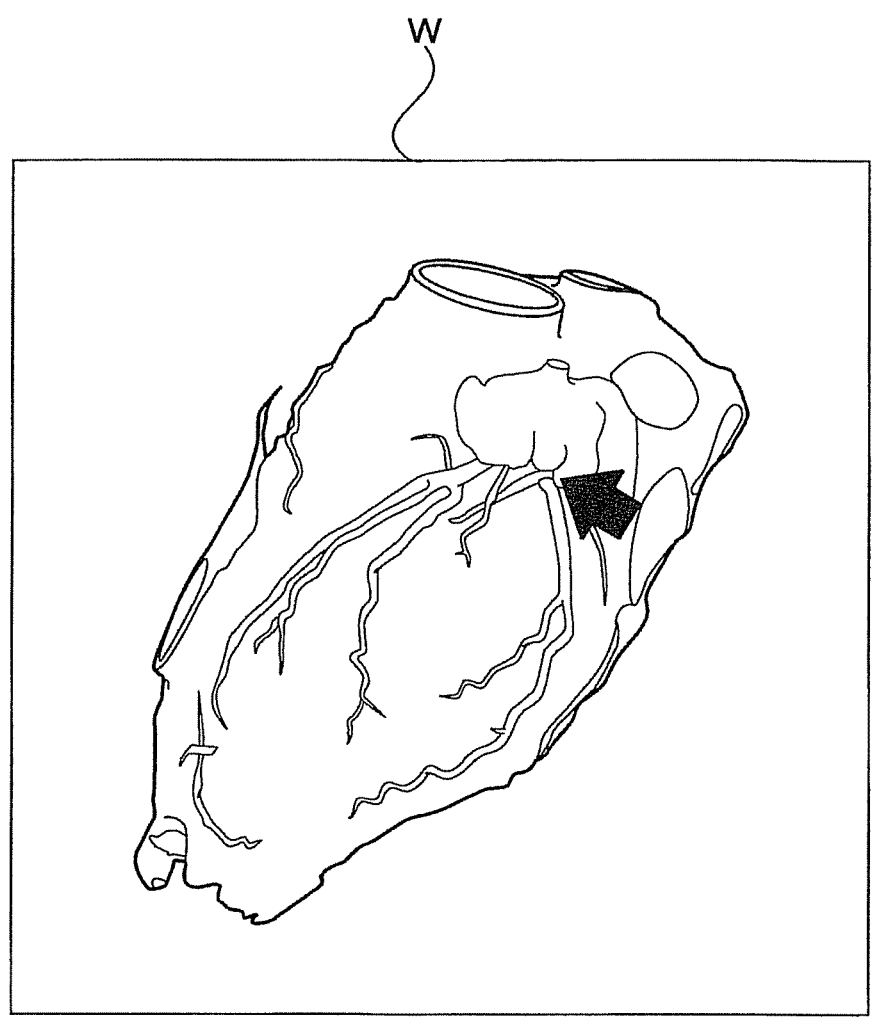
FIG. 8B is an example of a volume rendering image used in explanation of the fourth embodiment.

As shown in FIG. 8A, for cases in which radiographic image interpretation is performed on an attention site (refer to the arrows in FIG. 8A), using a volume rendering image (hereinafter may be referred to as a "VR image") based on the volume data, the VR image may be rotated in order to observe the attention site from an arbitrary direction. At this time, the position of the attention site on a display screen W of the display 11 changes (refer to the arrows in FIG. 8B, noting that in FIG. 8B, only blood vessels are displayed). Therefore, even if a radiographic interpreter designates an attention site in the VR image as the attention point, for cases in which the VR image is rotated, the position of the attention point also changes according to changes in the position of the attention site. In the present embodiment, even in cases of this type, the configuration in which the region including the attention point can be extracted is described.

As shown in FIG. 9, the medical image archiving apparatus 5 includes a specification part 26. Based on the information of the attention point in the VR image designated at the designating part 14, in the volume data, which serves as the basis for the VR image, the specification part 26 specifies a 3-dimensional coordinate value that corresponds to the attention point. Moreover, for cases in which the VR image is rotated, the specification part 26 calculates to what extent the 3-dimensional coordinate value of the attention point changed and specifies a new 3-dimensional coordinate value. Furthermore, the specification part 26 calculates the attention point in the VR image corresponding to the new 3-dimensional coordinate value.

For example, the VR image as shown in FIG. 8A is displayed on the display 11 of the medical image utilization apparatus 8. When the radiographic interpreter inputs the attention point (refer to the arrows in FIG. 8A) in the image, the designating part 14 designates the attention point in the VR image based on the input. The information of the designated attention point is transmitted through the transmission part 15 and the reception part 16 to the specification part 26.

Based on the information of the attention point, in the volume data, the specification part 26 specifies the 3-dimensional coordinate value corresponding to the attention point. The specified value, for example, is stored in the storage part, not shown in the figures.

Subsequently, for cases in which the radiographic interpreter inputs a command to rotate the VR image displayed on the medical image utilization apparatus 8, the specification part 26 specifies a new 3-dimensional coordinate value, by, based on the input information, calculating to what extent the previously specified 3-dimensional coordinate value changed as a result of the rotation. Furthermore, the specification part 26 specifies a coordinate value in the VR image corresponding to this new 3-dimensional coordinate.

The coordinate value specified by the specification part 26 is transmitted to the extraction part 19, and based on this coordinate value, extraction processing by the extraction part 19 is executed.

In this way, according to the configuration of the present embodiment, even for cases in which the attention point moves on the display 11, with regard to the region (extraction region) corresponding to the attention point, it is possible to observe high resolution movie images at the requested frame rate.

(Fifth Embodiment)

Figure 10:
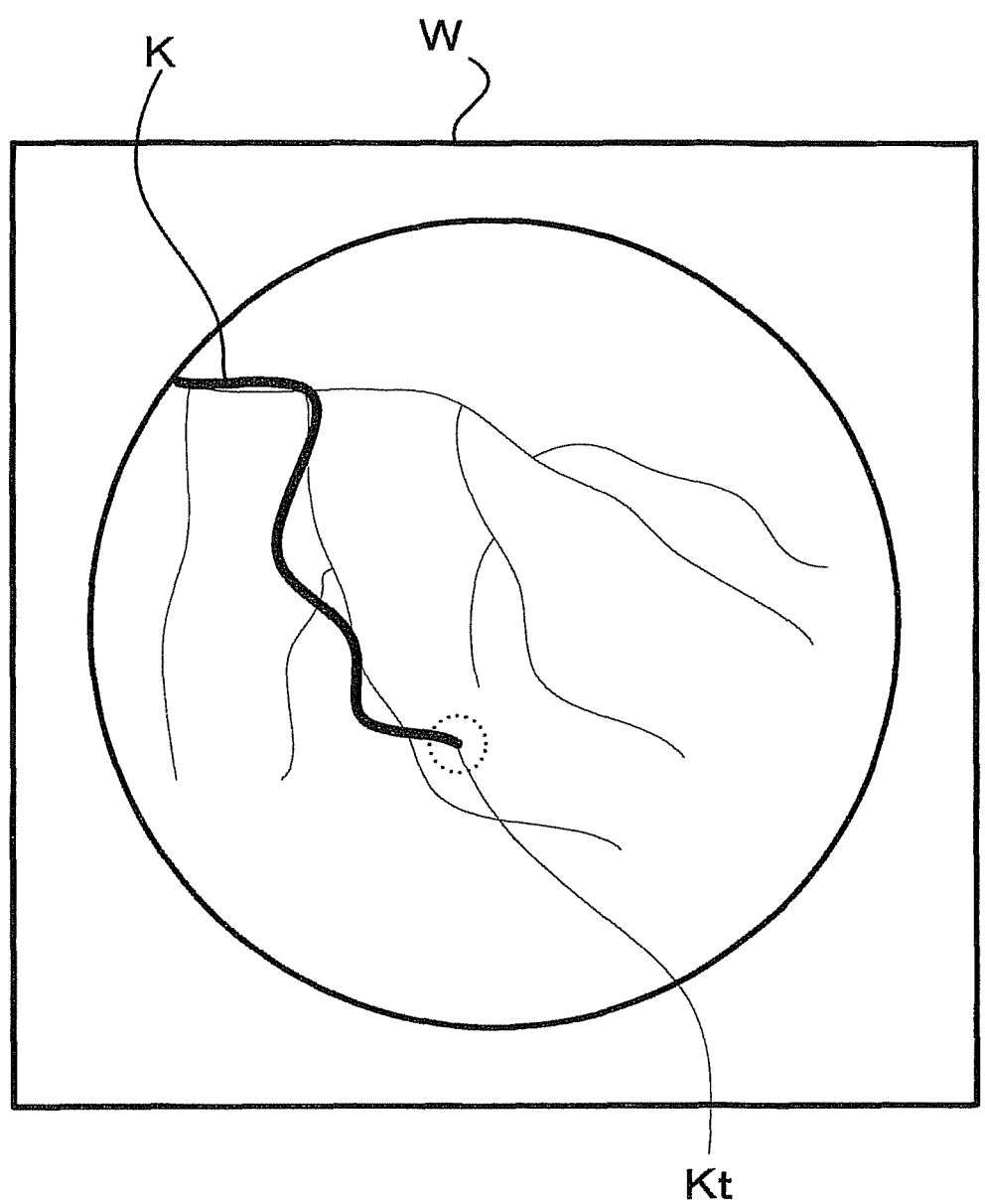
FIG. 10 is an example of an image used in explanation of the fifth embodiment.

Next, using FIG. 10, processing according to the fifth embodiment is explained in detail. Moreover, in the present embodiment, the configuration of the first embodiment is explained below as a basis; however, the configuration of the present embodiment is also applicable to the second embodiment and the third embodiment.

Moreover, an explanation for the configuration, which is the same as the first embodiment, is omitted.

As shown in FIG. 10, there is a procedure by which, while taking an X-ray image of some regions, such as the heart, treatment is performed by inserting a catheter K into the blood vessel that is displayed there. At this time, because attention is paid to the movement of a catheter tip Kt, a radiographic interpreter may designate the catheter tip Kt as the attention point (refer to the dotted circle in FIG. 10). However, even if the catheter tip Kt is designated as the attention point in the image displayed on the display screen W of the display 11, the catheter K moves according to the procedure. That is, the attention point moves. In the present embodiment, the configuration is described in which even for cases of this type, the region including the attention point can be extracted.

As is the case with the fourth embodiment, the medical image archiving apparatus 5 in the present embodiment includes the specification part 26. Based on the attention site designated by the designating part 14, the specification part 26 in the present embodiment specifies the position corresponding to the attention site in the image displayed on the display 11. For example, for cases in which the "catheter tip" is. designated as the attention site by the designating part 14, the specification part 26 specifies the coordinates of the catheter tip in the displayed image. Note that for the designation of the catheter tip in the image, known procedures such as Japanese Unexamined Patent Application H05-161634, Japanese Unexamined Patent Application Publication 2008-264254, and Japanese Unexamined Patent Application Publication 2000-175897 can be applied. Moreover, for the designation of the attention site, for example, some items (for example, the "catheter tip," "coronary artery," etc.) are displayed on the display screen, and among these, arbitrary item may be selected or the name of the attention site may be directly input.

The coordinate value specified by the specification part 26 is transmitted to the extraction part 19, and extraction processing by the extraction part 19 is executed based on this coordinate value.

In this way, according to the configuration of the present embodiment, even for cases in which the attention point moves on the display 11, with regard to the region (extraction region) corresponding to the attention point, it is possible to observe high resolution movie images at the requested frame rate.

(Common Items for the First Embodiment to the Fifth Embodiment)

Even cases in which multiple attention points are designated can be achieved by performing the same processing as the embodiments.

Moreover, using the input means, not shown in the figures, etc., it is also possible to specify in advance whether priority is to be placed on the requested frame rate or on the extraction region.

For example, cases in which the radiographic interpreter wishes to view the image of the entire heart at some requested frame rate are considered. In this case, depending on the performance of the medical image utilization apparatus 8, it is possible that the entire heart region may not be extracted as the extraction region, or that the requested frame rate is not met.

In such cases, for example, if priority is placed on the extraction region (the entire heart as the subject), resulting from the input means, not shown in the figures, it is determined whether or not the requested frame rate desired by the radiographic interpreter is appropriate for displaying the subject at high resolution, and for cases in which it is determined as inappropriate, it is also possible to provide an automatic calculating part that automatically calculates the optimal frame rate with displaying the entire heart in the medical image utilization apparatus 8. The automatic calculating part is one example of a "determination part" and a "calculating part."

In contrast, if priority is placed on the requested frame rate, resulting from the input means, not shown in the figures, for the automatic calculating part, it is determined whether or not the requested frame rate desired by the radiographic interpreter is appropriate for displaying the entire heart at high resolution, and for cases in which it is determined as inappropriate, processing to automatically calculate the extraction region according to the requested frame rate is performed.

While certain embodiments have been described, these embodiments have been presented by way of example only, and are not intended to limit the scope of the inventions. Indeed, the novel systems described herein may be embodied in a variety of their forms; furthermore, various omissions, substitutions and changes in the form of the systems described herein may be made without departing from the spirit of the inventions. The accompanying claims and their equivalents are intended to cover such forms or modifications as would fall within the scope and spirit of the inventions.

What is claimed is:

1. A medical image apparatus, comprising a medical image utilization apparatus and a medical image archiving apparatus, said medical image utilization apparatus comprising:
an acquisition part configured to acquire a requested frame rate for cases in which a plurality of medical images taken with a medical imaging apparatus are movie displayed on a display of said medical image utilization apparatus; and
a designating part configured to designate an attention point with respect to one of said plurality of medical images displayed on said display,
and said medical image archiving apparatus comprising:
a transmission speed measurement part that measures the data transmission speed between said medical image utilization apparatus and said medical image archiving apparatus;
an extraction part, based on said requested frame rate, said attention point, and said data transmission speed, configured to extract a region including said attention point, for each of said plurality of medical images; and
a transmission part configured to transmit an image of the region extracted by said extraction part to said display,
wherein said display is configured to display one of the plurality of medical images as a static image and display, as a moving image, the images of the region extracted from the static image by said extraction part at said requested frame rate.

2. The medical image apparatus according to claim 1, wherein
said extraction part calculates the size of said region, based on said requested frame rate and said data transmission speed, and determines the position of said region for each of said plurality of medical images, based on said size and said attention point.

3. A medical image apparatus, comprising a medical image utilization apparatus and a medical image archiving apparatus,
said medical image utilization apparatus comprising:
an acquisition part configured to acquire a requested frame rate for cases in which a plurality of medical images taken with a medical imaging apparatus are movie displayed on a display of said medical image utilization apparatus; and
a designating part configured to designate an attention point with respect to one of said plurality of medical images displayed on said display; and
an actual frame rate measuring part configured to measure an actual frame rate when some of said plurality of medical images are movie displayed on said display,
and said medical image archiving apparatus comprising:
an extraction part configured to, based on said requested frame rate, said attention point, and said actual frame rate, extract a region including said attention point, for each of said plurality of medical images; and
a transmission part configured to transmit an image of the region extracted by said extraction part to said medical image utilization apparatus,
wherein said display is configured to display one of the plurality of medical images as a static image and display, as a moving image, the images of the region extracted from the static image by said extraction part at said requested frame rate.

4. The medical image apparatus according to any one of claim 1 to claim 3, comprising a control part, before movie displaying in the region extracted by said extraction part at said requested frame rate, controls so as to display the information indicating the region extracted by said extraction part on medical images displayed on said display.

5. A medical image apparatus, comprising a medical image utilization apparatus and a medical image archiving apparatus,
said medical image utilization apparatus comprising:
an acquisition part configured to acquire a requested frame rate for case in which a plurality of medical images taken with a medical imaging apparatus are movie displayed on a display of said medical image utilization apparatus; and
a designating part configured to designate an attention point with respect to one of said plurality of medical images displayed on said display; and
an actual frame rate measuring part configured to measure an actual frame rate when some of said plurality of medical images are movie displayed on said display,
and said medical image archiving apparatus comprising:
an extraction part configured to, based on said requested frame rate, said attention point, and said actual frame rate, extract the region including said attention point, for each of said plurality of medical images; and
a transmission part configured to transmit an image of the region extracted by said extraction part to said medical image utilization apparatus,
wherein said display is configured to display, as a moving image, the images of the region extracted by said extraction part at said requested frame rate, and said extraction part, based on said requested frame rate and said actual frame rate, sets a search range of the extraction region.

6. The medical image apparatus according to claim 5, wherein said extraction part, before the extraction region is determined, in advance, sets said search range and sets the intermediary value of said search range as the temporary extraction region, and if said requested frame rate and said actual frame rate match each other, said extraction part determines said temporary extraction region as said extraction region.

7. The medical image apparatus according to claim 6, wherein said extraction part, if said actual frame rate exceeds said requested frame rate, determines a new search range, which is between the intermediary value and the minimum value of said search range, and determines the intermediary value of said new search range as a new temporary extraction region.

8. The medical image apparatus according to claim 1, comprising:
a determination part that determines whether or not the requested frame rate acquired by said acquisition part is appropriate for the movie display of said plurality of medical images; and
a calculation part that, if it is determined to be inappropriate by said determination part, calculates the optimal frame rate for the movie display of said plurality of medical images.

9. The medical image apparatus according to claim 1, comprising:
a determination part that determines whether or not the requested frame rate acquired by said acquisition part is appropriate for the movie display of said plurality of medical images; and
a calculation part that, if it is determined to be inappropriate by said judgment part, calculates an extraction region appropriate for said requested frame rate.

10. A medical image archiving apparatus, comprising:
a transmission speed measurement part that measures data transmission speed with respect to a medical image utilization apparatus;

an extraction part that, based on a requested frame rate for cases in which a plurality of medical images taken with a medical imaging apparatus are movie displayed on a display of said medical image utilization apparatus, an attention point designated with respect to one of said plurality of medical images displayed on said display, and said data transmission speed, extracts a region including said attention point, for each of said plurality of medical images; and a transmission part that transmits an image of the region extracted by said extraction part to said display, wherein said display is configured to display one of the plurality of medical images as a static image and display, as a moving image, the images of the region extracted from the static image by said extraction part at said requested frame rate.

* * * * *